United States Patent [19]

Kott et al.

[11] Patent Number: 5,641,739
[45] Date of Patent: Jun. 24, 1997

[54] AQUEOUS DETERGENT COMPOSITIONS CONTAINING CHELANTS WHICH REMAIN UNDISSOLVED UNDER ACIDIC CONDITIONS

[75] Inventors: Kevin Lee Kott; Alan David Willey, both of Cincinnati, Ohio

[73] Assignee: The Procter & Gamble Company, Cincinnati, Ohio

[21] Appl. No.: 431,869

[22] Filed: May 1, 1995

[51] Int. Cl.$^6$ .................. C11D 3/33; C11D 3/39; C11D 3/395; C11D 17/08

[52] U.S. Cl. ............ 510/372; 252/186.27; 252/186.28; 252/186.29; 510/303; 510/310; 510/318; 510/376; 510/418; 510/434; 510/480

[58] Field of Search ............... 510/303, 310, 510/318, 372, 376, 418, 434, 480; 252/186.27, 186.28, 186.29

[56] References Cited

U.S. PATENT DOCUMENTS

| | | | |
|---|---|---|---|
| 3,632,637 | 1/1972 | Martell | 510/480 |
| 4,225,452 | 9/1980 | Leigh | 510/480 |
| 4,325,828 | 4/1982 | Postlethwaite | 510/480 |

FOREIGN PATENT DOCUMENTS

| | | |
|---|---|---|
| 0 037 146 | 10/1981 | European Pat. Off. . |
| 0 331 556 | 9/1989 | European Pat. Off. . |
| 90/02339 | 3/1990 | WIPO . |

*Primary Examiner*—Dennis Albrecht
*Attorney, Agent, or Firm*—Michael D. Jones; Brian M. Bolam; Kim W. Zerby

[57] ABSTRACT

Aqueous, acidic bleach laundry detergent compositions with selected chelants which remain substantially undissolved in the acidic product formulation are described. The chelants are chemically stable within the product even upon extended storage and provide improved in-use chelating as well as product performance.

16 Claims, No Drawings

AQUEOUS DETERGENT COMPOSITIONS CONTAINING CHELANTS WHICH REMAIN UNDISSOLVED UNDER ACIDIC CONDITIONS

FIELD OF THE INVENTION

The present invention relates to aqueous, acidic bleach laundry detergent compositions with selected chelants which remain substantially undissolved in the acidic product formulation. The chelants are chemically stable within the product even upon extended storage and provide improved in-use chelating as well as product performance.

BACKGROUND OF THE INVENTION

It is common practice for formulators of detergent compositions to include bleaching agents such as hydrogen peroxide or sources thereof in such compositions for their bleaching effect. Such bleaches are widely recognized for their ability to remove various stains and soils from fabrics. It is also common practice to include a chelant in such detergent compositions. Chelants act to scavenge certain metal ions commonly found in wash water. Since the presence of these metal ions can inhibit the performance of many detergent additives, the addition of a chelant to a detergent composition acts to enhance the performance of the other detergent additives. Unfortunately, hydrogen peroxide has a tendency to oxidize chelants when both the chelant and source of hydrogen peroxide are formulated in a detergent formulation, especially liquid formulations, rendering the chelant much less effective in the wash.

It has now been determined that certain selected chelants provide unexpectedly effective product performance in the wash. The preferred chelants also have greatly increased chemical stability within an aqueous detergent composition. Without being limited by theory, it is believed that the chelants remain substantially undissolved in the acidic detergent composition, thereby inhibiting the oxidation of the chelant by hydrogen peroxide. Importantly, it is believed that these chelants become highly water soluble at typical alkaline wash pH's (from about 7 to abut 10.5) and thus function very effectively in use.

When formulated as described herein, aqueous detergent compositions are provided using the selected chelants to enhance product performance with excellent results. Advantages of these embodiments include excellent performance at typical wash pH's, e.g., about 7–10.

BACKGROUND ART

See for example, U.S. Pat. No. 4,325,828, Postlethwaite, issued Apr. 20, 1982, U.S. Pat. No. 4,225,452, Leigh, issued Sep. 30, 1980, and GB 2,113,730, Leigh, published Aug. 10, 1983.

SUMMARY OF THE INVENTION

The present invention relates to chelants suitable for use in aqueous, acidic laundry detergent compositions. More specifically, the present invention relates to a liquid, aqueous detergent composition having a pH of below about 7 and comprising a chelant which remains substantially insoluble at a pH of below about 7 and which is water-soluble at alkaline pH. Said chelant has a stability constant for iron(3+) of at least log k equal to about 10, more preferably 20 at a temperature of 25° C. and an ionic strength of 0.1. Further, said chelant preferably has a stability constant for copper of at least log k equal to about 10, more preferably 20 at a temperature of 25° C. and an ionic strength of 0.1. Stability constants are further defined in Martell, A. E.; Smith, R. M. *Critical Stability Constants*, Plenum Press: New York, 1974; Volume 1.

The aqueous detergent compositions of the present invention have a pH of below about 7, preferably from about 3 to about 7, and comprise:

a) an effective amount of a source of hydrogen peroxide; and b) a chelating effective amount, preferably from about 0.05% to about 5% by weight of detergent composition, of a chelant, which is substantially undissolved at the pH of said detergent composition, of the formula

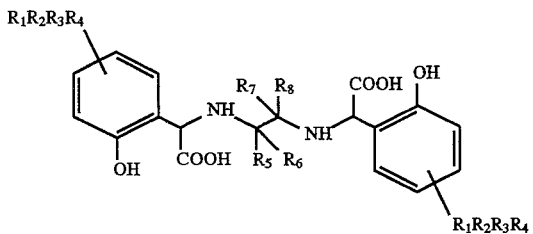

wherein $R_1$, $R_2$, $R_3$, and $R_4$ are independently selected from the group consisting of —H, alkyl, alkoxy, aryl, aryloxy, —Cl, —Br, —NO$_2$, —C(O)R', and —SO$_2$R"; wherein R is selected from the group consisting of —H, —OH, alkyl, alkoxy, aryl, and aryloxy; R" is selected from the group consisting of alkyl, alkoxy, aryl, and aryloxy; and $R_5$, $R_6$, $R_7$, and $R_8$ are independently selected from the group consisting of —H and alkyl.

Preferably, $R_1$, $R_2$, $R_3$, and $R_4$ are independently selected from the group consisting of —H, alkyl, and alkoxy; and $R_5$, $R_6$, $R_7$, and $R_8$ are independently selected from the group consisting of —H and methyl. More preferably, $R_1$, $R_2$, $R_3$, and $R_4$ are independently selected from the group consisting of —H and methyl; and $R_5$, $R_6$, $R_7$, and $R_8$ are —H.

The liquid, aqueous detergent compositions of this invention may further comprise optional conventional detersive additives, including one or more bleach activators. Examples of suitable bleach activators include acylated trialkylcitrates, N-acyl caprolactams, N-acyl valerolactams, amido-derived bleach activators, tetraacetyl ethylene diamine, acylated glycerols, N-acyl glycine anhydrides, and alkanoyloxybenzenesulfonates. Most preferred are those bleach activators selected from the group consisting of acylated trialkylcitrates, acyl caprolactams, acyl valerolactams, and mixtures thereof. Other optional conventional detersive additives include surfactants, builders, inorganic stabilizers, antioxidants or radical scavengers, secondary conventional chelants, preferably selected from the group consisting of diethylene triamine pentaacetic acid (DTPA), diethylene triamine penta(methylene phosphonic acid), sulfonated ethylenebis(2-hydroxyphenyl)glycine, and mixtures thereof.

All percentages, ratios, and proportions are by weight, unless otherwise specified. All documents cited are incorporated herein by reference.

DETAILED DESCRIPTION OF THE INVENTION
Illustrations of preferred chelant structures include:
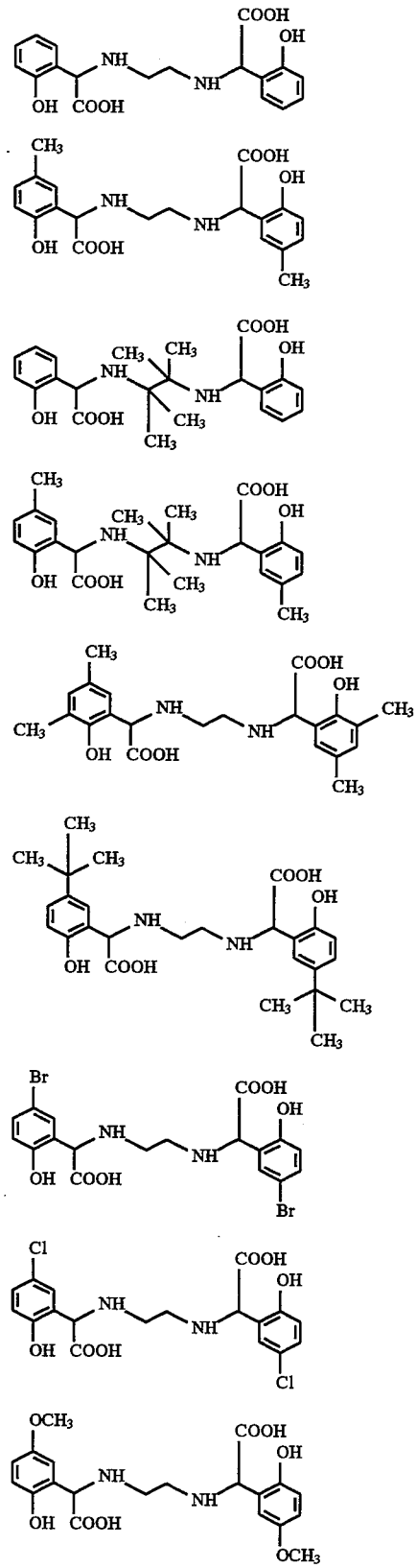
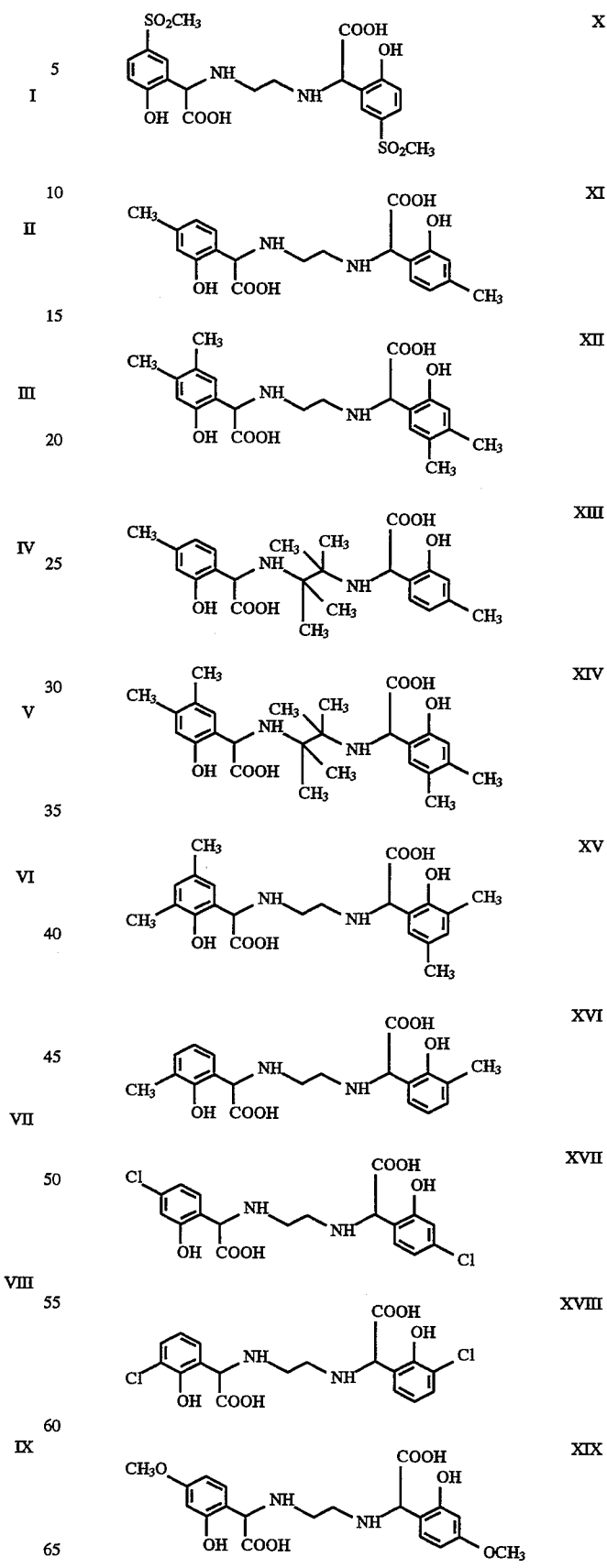

-continued

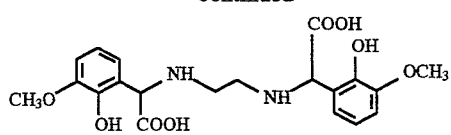

XX

Highly preferred chelants are of the structures:

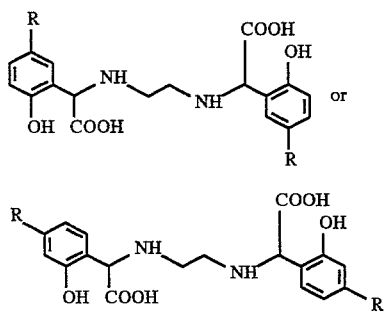

wherein each R is independently selected from the group consisting of —H, —CH$_3$, C$_2$–C$_9$ alkyl, and mixtures thereof. Examples of these highly preferred chelants are:

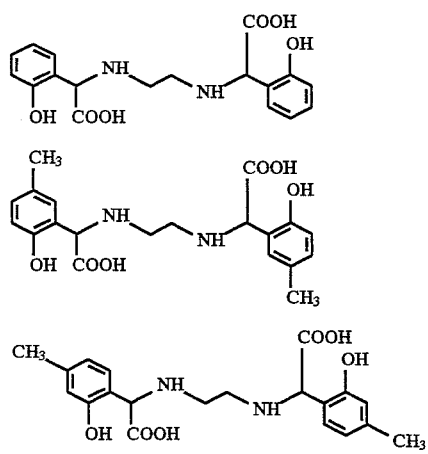

In preferred embodiments, the chelants are in particle form and should be of sufficient size to be suspended in an aqueous medium. Thus, the chelants herein preferably have a particle size of from about 0.1 to about 1,000 microns, preferably, from about 1 to about 500 microns, more preferably from about 1 to about 250 microns. Moreover, the liquid detergent compositions herein have a theology capable of suspending said chelant solids.

Rheoloy—Those skilled in the art will realise that, in the simplest case, a rheology capable of suspending solids is simply a viscosity sufficient to prevent settling, creaming, floeting, etc. of the particles being suspended. The required viscosity will vary according to particle size but should generally be greater than 300 cps (measured at 10 rpm) preferably greater than 600 cps and more preferably still greater than 1000 cps. It will further be realised by those skilled in the art that the rheology will preferably be that of a non-Newtonian, shear thinning fluid. Such fluids exhibit very high viscosities at low shear with viscosity reducing as shear is increased e.g. a shear thinning fluid may have a viscosity of 2000 cps at 10 rpm but only 500 cps at 100 rpm. Such shear thinning systems may be obtained in several ways including the use of associative polymeric thickeners, emulsions and specific surfactant systems.

The pH of the compositions herein may be adjusted to the desired pH of below about 7 by the addition of citric acid or any other suitable acidulants, such as sulfuric acid and hydrochloric acid.

The chelants of this invention can be synthesized according to the methods given in U.S. Pat. No. 4,130,582 or EP 331,556. A representative example is provided below.

Synthesis of Ethylenebis(2-hydroxyphenyl)glycine—In a 3-neck round bottom flask equipped with an addition funnel, reflux condenser and mechanical stirrer is placed 367 g of phenol (3.9 mol). After heating the reaction to 40°–45° C., 9.02 g of ethylenediamine (0.15 mol) and 18.0 g of 50% aqueous sodium hydroxide (0.23 mol) are added consecutively, each over a period often minutes. The reaction is then cooled back to 40°–45° C., and 44.4 g of 50% aqueous glyoxylic acid (0.3 mol) is added dropwise over 15 minutes while maintaining the temperature at 40°–45° C. The reaction mixture is then heated to 70°–75° C. for 2 hours.

The reaction is subsequently cooled to room temperature and diluted with 600 mL of H$_2$O and 1000 mL of CCl$_4$. The mixture is stirred vigorously, the layers separated, and the aqueous layer extracted twice with 600 mL CCl$_4$. The product is precipitated from the aqueous solution by adjusting the pH to 4 and cooling. The precipitate is then filtered and rinsed with cold H$_2$O to yield 60% of a product which is $\geq$95% of the ortho isomer.

Purification to remove colored impurities—The product obtained above is typically highly colored (orangish), and may be purified by stirring the product as a slurry at pH of 4 with 15% aqueous H$_2$O$_2$ at 70°–90° C. for at least 15 minutes. The white to off-white product which is then filtered is essentially free of colored impurities. The concentration of H$_2$O$_2$, the temperature, and the stirring time can vary widely while still providing effective results. The choice of oxidant can vary as well while still providing effective results. Preferred oxidizing agent are selected from the group consisting of organic peracids, peracetic acid, HNO$_3$, KMnO$_4$, a source of hydrogen peroxide, hydrogen peroxide, and mixtures thereof.

Thus, in the above synthesis procedure, the precipitate can be easily purified of color impurities by stirring with H$_2$O$_2$ as described here immediately before filtering.

Thus, a preferred purification process for removing color impurities from the chelants of this invention comprises:

i) a chelant compound of the structure:

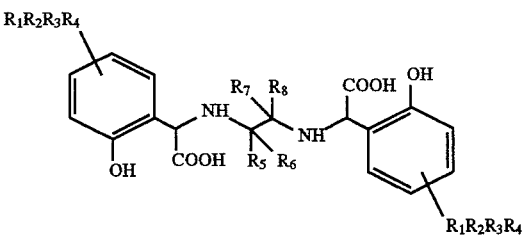

wherein R$_1$, R$_2$, R$_3$, and R$_4$ are independently selected from the group consisting of —H, alkyl, alkoxy, aryl, aryloxy, —Cl, —Br, —NO$_2$, —C(O)R', and —SO$_2$R"; further wherein R' is selected from the group consisting of —H, —OH, alkyl, alkoxy, aryl, and aryloxy; R" is selected from the group consisting of alkyl, alkoxy, aryl, and aryloxy; and R$_5$, R$_6$, R$_7$, and R$_8$ are independently selected from the group consisting of —H and alkyl; and (ii) impurities formed during the preparation of said chelant compound; said process comprising the steps of:

1) mixing said chelant and impurities composition with a water-soluble oxidizing agent to form a heterogeneous solution at a pH of about 3 to about 5;
2) recovering said chelant free of color impurities.

Alteratively, the purification can be conducted in aqueous alkaline solution, preferably at a pH of from about 8 to about 10, using a mild reducing agent such as sodium bisulfite. The concentration of reductant, the temperature, and the stirring time may vary widely while still providing effective results.

Thus, an alternative process for removing color impurities from the chelants of this invention comprises:

i) a chelant compound of the structure:

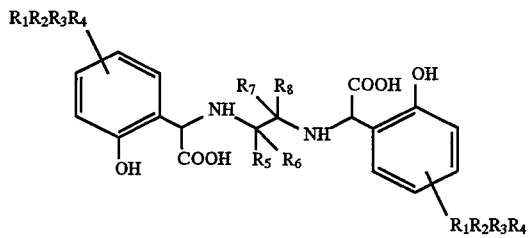

wherein $R_1$, $R_2$, $R_3$, and $R_4$ are independently selected from the group consisting of —H, alkyl, alkoxy, aryl, aryloxy, —Cl, —Br, —$NO_2$, —C(O)R', and —$SO_2R''$; further wherein R' is selected from the group consisting of—H, —OH, alkyl, alkoxy, aryl, and aryloxy; R" is selected from the group consisting of alkyl, alkoxy, aryl, and aryloxy; and $R_5$, $R_6$, $R_7$, and $R_8$ are independently selected from the group consisting of —H and alkyl; and (ii) impurities formed during the preparation of said chelant compound; said process comprising the steps of:
 a) mixing said chelant and impurities composition with a water-soluble reducing agent to form a homogeneous solution at a pH of above about 7; and
 b) adjust the pH of the solution of a) to a pH of below about 7; and
 c) recovering said chelant free of color impurities.

Hydrogen Peroxide Source: Types, Levels, and Modes of Use—A source of hydrogen peroxide herein is any convenient compound or mixture which under consumer use conditions provides an effective amount of hydrogen peroxide. Hydrogen peroxide, itself, is highly preferred. Levels may vary widely and are typically from about 0.5% to about 70%, more typically from about 0.5% to about 25%, by weight of the detergent compositions herein.

The source of hydrogen peroxide used herein can be any convenient source. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Mixtures of any convenient hydrogen peroxide sources can also be used.

Organic Stabilizers—The compositions herein may also optionally contain organic stabilizers for improving the chemical stability of the composition, provided that such materials are compatible or suitably formulated. Organic stabilizers are antioxidants or radical scavengers which can be selected from the following group: monophenols such as 2,6-di-tert-butylphenol or 2,6-di-tert-butyl-4-methylphenol; diphenols such as 2,2'-methylenebis(4-methyl-6-tert-butylphenol) or 4,4'-methylenebis(2,6-di-tert-butylphenol); polyphenols such as 1,3,5-trimethyl-2,4,6-tris(3',5'-di-tert-butyl-4-hydroxybenzyl)benzene; hydroquinones such as 2,5-di-tert-amylhydroquinone or tert-butylhydroquinone; aromatic amines such as N-phenyl-N: (1,3-dimethylbutyl)-p-phenylenediamine or N-phenyl-α-napthylamine; dihydroquinolines such as 2,2,4-trimethyl-1,2-dihydroquinoline; and mixtures thereof. A more complete illustration of antioxidants or radical scavengers is given the Kirk-Othmer Encyclopedia of Chemical Technology, $4^{th}$ edition, Kroschwitz, J. I., Howe-Grant, M., Eds.; Wiley: New York, 1992; Volume 3, p440–445. Organic stabilizers are typically used in the present compositions at levels from 0.01% to 5.0%, more preferably from 0.1% to 0.5%.

Inorganic Stabilizers—Examples on inorganic stabilizers include: sodium stannate and various alkali metal phosphates such as the well-known sodium tripolyphosphates, sodium pyrophosphate and sodium orthophosphate, ethane-1-hydroxy-1,1-diphosphonate and other known phosphonates (see, for example, U.S. Pat. Nos. 3,159,581; 3,213,030; 3,422,021; 3,400,148 and 3,422,137).

Other Conventional Ingredients for Cleaning Compositions—Fully-formulated aqueous, liquid laundry detergent compositions typically will also comprise other optional conventional detergent ingredients to improve or modify performance. Typical, non-limiting examples of such ingredients are disclosed hereinaPter for the convenience of the formulator.

Conventional Detergent Ingredients

Bleach catalysts—If desired, detergent compositions herein may additionally incorporate a catalyst or accelerator to further improve performance. Any suitable bleach catalyst can be used. Typical bleach catalysts comprise a transition-metal complex, open one wherein the metal co-ordinating ligands are quite resistant to labilization and, optionally, coated. Such catalyst compounds often have features of naturally occurring compounds but are principally provided synthetically and include, for example, the manganese-based catalysts disclosed in U.S. Pat. Nos. 5,246,621, 5,244,594; 5,194,416; 5,114,606; and European Pat. App. Pub. Nos. 549,271A1, 549,272A1, 544,440A2, and 544,490A1; preferred examples of these catalysts include $Mn^{IV}_2(u\text{-}O)_3$ (1,4,7-trimethyl-1,4,7-triazacyclononane)$_2$-(PF$_6$)$_2$, $Mn^{III}_2$ (u-O)$_1$(u-OAc)$_2$(1,4,7-trimethyl-1,4,7-triazacyclononane)$_2$ (ClO$_4$)$_2$, $Mn^{IV}_4$(u-O)$_6$(1,4,7-triazacyclononane)$_4$(ClO$_4$)$_4$, $Mn^{III}$-$Mn^{IV}_4$-(u-O)$_1$(u-OAc)$_2$-(1,4,7-trimethyl-1,4,7-triazacyclo-nonane)$_2$-(ClO$_4$)$_3$, $Mn^{IV}$-(1,4,7-trimethyl-1,4,7-triazacyclo-nonane)-(OCH$_3$)$_3$(PF$_6$), and mixtures thereof; though alternate metal-co-ordinating ligands as well as mononuclear complexes are also possible and monometallic as well as di- and polymetallic complexes, and complexes of alternate metals such as iron are all within the present scope. Other metal-based bleach catalysts include those disclosed in U.S. Pat. Nos. 4,430,243 and 5,114,611. The use of manganese with various complex ligands to enhance bleaching is also reported in the following U.S. Pat. Nos.: 4,728,455; 5,284,944; 5,246,612; 5,256,779; 5,280,117; 5,274,147; 5,153,161; and 5,227,084.

Said manganese can be precomplexed with ethylenediaminedisuccinate or separately added, for example as a sulfate salt, with ethylenediaminedisuccinate. (See U.S. application Ser. No. 08/210,186, filed Mar. 17, 1994.) Other preferred transition metals in said transition-metal-containing bleach catalysts include iron or copper.

As a practical matter, and not by way of limitation, the bleaching compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 50 ppm, of the catalyst species in the laundry liquor.

Conventional Bleach Activators—"Conventional bleach activators" herein are any bleach activators which are compatible with liquid laundry detergent compositions herein. Numerous conventional bleach activators are known and are optionally included in the instant cleaning compositions. Various nonlimiting examples of such activators are disclosed in U.S. Pat. No. 4,915,854, issued Apr. 10, 1990 to Mao et al., and U.S. Pat. No. 4,412,934. Tetraacetylethylenediamine (TAED) activators are typical. See also U.S. Pat. No. 4,634,551 for other typical conventional bleach activators.

Highly preferred amido-derived bleach activators are those of the formulae:

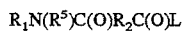

or

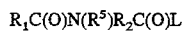

wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. A leaving group is any group that is displaced from the bleach activator as a consequence of the nucleophilic attack on the bleach activator by the perhydrolysis anion. A preferred leaving group is phenyl sulfonate.

Preferred examples of bleach activators of the above formulae include (6-octanamido-caproyl) oxybenzenesulfonate, (6-nonanamidocaproyl) oxybenzenesulfonate, (6-decanamido-caproyl) oxybenzenesulfonate, and mixtures thereof as described in U.S. Pat. No. 4,634,551, incorporated herein by reference.

Another class of bleach activators comprises the benzoxazin-type activators disclosed by Hodge et al in U.S. Pat. No. 4,966,723, issued Oct. 30, 1990, incorporated herein by reference. A highly preferred activator of the benzoxazin-type is:

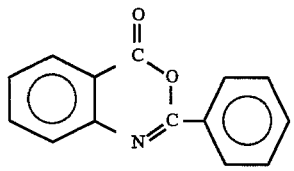

Still another class of preferred bleach activators includes the acyl lactam activators, especially acyl caprolactams and acyl valerolactams of the formulae:

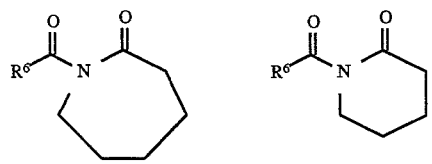

wherein $R^6$ is H, an alkyl, aryl, alkoxyaryl, or alkaryl group containing from 1 to about 12 carbon atoms, or a substituted phenyl group containing from about 6 to about 18 carbons.

See copending U.S. application Ser. Nos. 08/064,562 and 08/082,270, which disclose substituted benzoyl lactams. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactarn, substituted benzoyl lactams, and mixtures thereof. See also U.S. Pat. No. 4,545,784, issued to Sanderson, Oct. 8, 1985, incorporated herein by reference, which discloses acyl caprolactams, including benzoyl caprolactam, adsorbed into sodium perborate.

Bleaching agents other than hydrogen peroxide sources are also known in the art and can be utilized herein as adjunct ingredients. One type of non-oxygen bleaching agent of particular interest includes photoactivated bleaching agents such as the sulfonated zinc and/or aluminum phthalocyanines. See U.S. Pat. No. 4,033,718, issued Jul. 5, 1977 to Holcombe et at. If used, detergent compositions will typically contain from about 0.025% to about 1.25%, by weight, of such bleaches, especially sulfonated zinc phthalocyanine.

Organic peroxides, especially diacyl peroxides are extensively illustrated in Kirk Othmer, Encyclopedia of Chemical Technology, Vol. 17, John Wiley and Sons, 1982 at pages 27–90 and especially at pages 63–72, all incorporated herein by reference. Suitable organic peroxides, especially diacyl peroxides, are further illustrated in "Initiators for Polymer Production", Akzo Chemicals Inc., Product Catalog, Bulletin No. 88–57, incorporated by reference. Preferred diacyl peroxides herein whether in pure or formulated form for granule, powder or tablet forms of the bleaching compositions constitute solids at 25° C., e.g., CADET® BPO 78 powder form of dibenzoyl peroxide, from Akzo. Highly preferred organic peroxides, particularly the diacyl peroxides, for such bleaching compositions have melting points above 40° C., preferably above 50° C. Additionally, preferred are the organic peroxides with SADT's (as defined in the foregoing Akzo publication) of 35° C. or higher, more preferably 70° C. or higher. Nonlimiting examples of diacyl peroxides useful herein include dibenzoyl peroxide, lauroyl peroxide, and dicumyl peroxide. Dibenzoyl peroxide is preferred. In some instances, diacyl peroxides are available in the trade which contain oily substances such as dioctyl phthalate.

The present compositions can optionally further comprise conventional, known quaternary substituted bleach activators (QSBA). QSBA's are further illustrated in U.S. Pat. No. 4,539,130, Sep. 3, 1985 and U.S. Pat. No. 4,283,301. British Pat. 1,382,594, published Feb. 5, 1975, discloses a class of QSBA's optionally suitable for use herein. U.S. Pat. No. 4,818,426 issued Apr. 4., 1989 discloses another class of QSBA's. Also see U.S. Pat. No. 5,093,022 issued Mar. 3, 1992 and U.S. Pat. No. 4,904,406, issued Feb. 27, 1990. Additionally, QSBA's are described in EP 552, 812 A1 published Jul. 28, 1993, and in EP 540,090 A2, published May 5, 1993.

Also suitable for use herein are peroxyacids. The peroxyacid will typically comprise from about 0.5 to about 20, preferably from about 1 to about 10, wt. % of the detergent composition. Preferred organic peroxyacids are selected from the group consisting of 4-nonyl-amino-4-oxoperoxybutyric acid; 6-(nonylamino)-6-oxoperoxycaproic acid (NAPAA); 1,12-diperoxydodecanedioic acid; heptyl sulfonylperpropionic acid; decylsulphonyl perpropionic acid; and heptyl-, octyl-, nonyl-, decyl-sulphonylperbutyric acids, and mixtures thereof.

Detersive Surfactants -Surfactants are useful herein for their usual cleaning power and may be included in preferred embodiments of the instant detergent compositions at the usual detergent-useful levels. Generally, surfactants will comprise from about 0.1% to about 50%, preferably from about 1% to about 30%, more preferably from about 5% to about 25%, by weight of the liquid detergent compositions herein.

Nonlimiting examples of surfactants useful herein include the conventional $C_{11}$–$C_{18}$ alkylbenzene sulfonates ("LAS") and primary, branched-chain and random $C_{10}$–$C_{20}$ alkyl sulfates ("AS"); the $C_{10}$–$C_{18}$ secondary alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium; unsaturated sulfates such as oleyl sulfate; the $C_{10}$–$C_{18}$ alkyl alkoxy sulfates ("AE$_x$S") especially those wherein x is from 1 to about 7; $C_{10}$–$C_{18}$ alkyl alkoxy carboxylates (especially the EO 1–5 ethoxycarboxylates); the $C_{10}$–$C_{18}$ glycerol ethers; the $C_{10}$–$C_{18}$ alkyl polyglycosides and their corresponding sulfated polyglycosides; and $C_{12}$–$C_{18}$ alpha-sulfonated fatty acid esters. Detersive surfactants may be mixed in varying proportions for improved surfactancy as is well-known in the art. Also optionally included in the compositions are conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxylate/propoxylates), $C_{12}$–$C_{18}$ betaines and sulfobetaines ("sultaines"), $C_{10}$–$C_{18}$ amine oxides, and the like, can also be included in the cleaning compositions, The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be employed. If high sudsing is desired, the branched-chain $C_{10}$–$C_{16}$ soaps may be used. Mixtures of anionic and nonionic surfactants are especially useful. Automatic dishwashing compositions typically employ low sudsing suffactants, such as the mixed ethyleneoxy/propyleneoxy nonionics. Other conventional useful suffactants are listed in standard texts.

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. High performance compositions typically comprise from about 10% to about 80%, more typically from about 15% to about 50% by weight, of the detergent builder. Lower or higher levels of builder, however, are not excluded.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt or "overbased". When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulfonic acid, and carboxymethyloxysuccinic acid, the various alkali metal, ammonium and substituted ammonium salts of polyacetic acids such as nitrilotriacetic acid, as well as polycarb oxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance due to their availability from renewable resources and their biodegradability. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. Specific examples of succinate builders include: laurylsuccinate, myfistylsuecinate, palmitylsuecinate, 2-dodecenylsuceinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing in laundry compositions, which may need to be taken into account by the formulator.

Where phosphorus-based builders can be used, and especially in hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used though such materials are more commonly used in a low-level mode as chelants or stabilizers.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulfates, and aluminosilicates.

Secondary Chelating Agents—The compositions herein may also optionally contain a secondary transition-metal selective sequestrants or "chelating agents", e.g., iron and/or copper and/or manganese chelating agents, provided that such materials are compatible or suitably formulated. Chelating agents suitable for use herein can be selected from the group consisting of aminocarboxylates, phosphonates (especially the aminophosphonates), polyfunctionally-substituted aromatic chelating agents, and mixtures thereof Without intending to be bound by theory, it is believed that the benefit of these materials is due in part to their exceptional ability to remove iron, copper and manganese ions from washing solutions by formation of soluble chelates; other benefits include inorganic film prevention or scale inhibition. Commercial chelating agents for use herein include the DEQUEST® series, and chelants from Monsanto, DuPont, and Nalco, Inc.

Aminocarboxylates useful as optional chelating agents are further illustrated by ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts thereof.

In general, chelant mixtures may be used for a combination of functions, such as multiple transition-metal control, long-term product stabilization, and/or control of precipitated transition metal oxides and/or hydroxides.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A highly preferred biodegradable chelator for use herein is ethylenediamine disuccinate ("EDDS"), especially (but not limited to) the [S,S] isomer as described in U.S. Pat. No. 4,704,233, Nov. 3, 1987, to Hartman and Perkins. The trisodium salt is preferred though other forms, such as magnesium salts, may also be useful.

Aminophosphonates are also suitable for use as chelating agents in the compositions of the invention when at least low levels of total phosphorus are permitted in detergent compositions, and include the ethylenediaminetetrakis (methylenephosphonates) and the diethylenetriaminepentakis (methylenephosphonates). Preferably, these aminophos-phonates do not contain alkyl or alkenyl groups with more than about 6 carbon atoms.

If utilized, secondary chelating agents or transition-metal-selective sequestrants will preferably comprise from about 0.001% to about 10%, more preferably from about 0.05% to about 1% by weight of the compositions herein.

Enzymes—Enzymes can be included in the instant compositions for a wide variety of fabric laundering or other cleaning purposes, including removal of protein-based, carbohydrate-based, or triglyceride-based stains, for example, and for the prevention of refugee dye transfer, and for fabric restoration. The enzymes to be incorporated include proteases, amylases, lipases, cellulases, and peroxidases, as well as mixtures thereof Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders, etc.. In this respect bacterial or fungal enzymes are preferred, such as bacterial amylases and proteases, and fungat cellulases. The enzymes useful herein may optionally be coated for protection in the aqueous formulation.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of $B.$ $subtills$ and $B.$ $licheniformis$. Another suitable protease is obtained from a strain of $Bacillus$, having maximum activity throughout the pH range of 8–12, developed and sold by Novo Industries A/S as ESPERASE®. The preparation of this enzyme and analogous enzymes is described in British Patent Specification No. 1,243,784 of Novo. Proteolytic enzymes suitable for removing protein-based stains that are commercially available include those sold under the tradenames ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et al, published Jan. 9, 1985).

An especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76 in combination with one or more amino acid residue positions equivalent to those selected from the group consisting of +99, +101, +103, +107 and +123 in $Bacillus$ $amyloliquefaciens$ subtilisin as described in the patent applications of A. Baeck, C. K. Ghosh, P. P. Greycar, R. R. Bolt and L. J. Wilson, entitled "Protease-Containing Cleaning Compositions" having U.S. Ser. No. 08/136,797 (P&G Case 5040), and "Bleaching Compositions Comprising Protease Enzymes" having U.S. Ser. No. 08/136,626.

Amylases include, for example, α-amylases described in British Patent Specification No. 1,296,839 (Novo), RAPIDASE®, International Bio-Synthetics, Inc. and TERMAMYL®, Novo Industries.

Cellulases usable in the present invention include both bacterial or fungal cellulases. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from $Humicola$ $insolens$ and $Humicola$ strain DSM1800 or a cellulase 212-producing fungus belonging to the genus $Aeromonas$, and cellulase extracted from the hepatopancreas of a marine mollusk ($Dolabella$ $Auricula$ $Solander$). Suitable cellulases are also disclosed in GB-A-2.075.028; GB-A-2.095.275 and DE-OS-2.247.832. CAREZYME® (Novo) is especially useful.

Suitable lipase enzymes for detergent use include those produced by microorganisms of the Pseudomonas group, such as $Pseudomonas$ $stutzeri$ ATCC 19.154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum* var. lipolyticum NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*. The LIPOLASE® enzyme derived from *Humicola lanuginosa* and commercially available from Novo (see also EPO 341,947) is a preferred lipase for use herein.

Peroxidase enzymes can be used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

A wide range of enzyme materials and means for their incorporation into synthetic detergent compositions are also disclosed in U.S. Pat. No. 3,553,139, issued Jan. 5, 1971 to McCarty et at. Enzymes are further disclosed in U.S. Pat. No. 4,101,457, Place et at, issued Jul. 18, 1978, and in U.S. Pat. No. 4,507,219, Hughes, issued Mar. 26, 1985. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

Polymeric Soil Release Agent—Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

The polymeric soil release agents useful herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate:$C_3$ oxyalkylene terephthalate units is about 2:1 or lower, (ii) $C_4$–$C_6$ alkylene or oxy $C_4$–$C_6$ alkylene segments, or mixtures therein, (iii) poly (vinyl ester) segments, preferably polyvinyl acetate), having a degree of polymerization of at least 2, or (iv) $C_1$–$C_4$ alkyl ether or $C_4$ hydroxyalkyl ether substituents, or mixtures therein, wherein said substituents are present in the form of $C_1$–$C_4$ alkyl ether or $C_4$ hydroxyalkyl ether cellulose derivatives, or mixtures therein, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S$ $(CH_2)_nOCH_2CH_2O$—, where M is sodium and n is an integer from 4–6, as disclosed in U.S. Pat. No. 4,721,580, issued Jan. 26, 1988 to Gosselink. Polymeric soil release agents useful in the present invention also include eellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL (Dow). Cellulosic soil release agents for use herein also include those selected from the group consisting of $C_1$–$C_4$ alkyl and $C_4$ hydroxyalkyl cellulose; see U.S. Pat. No. 4,000,093, issued Dec. 28, 1976 to Nicol, et al.

Soil release agents characterized by poly(vinyl ester) hydrophobe segments include graft copolymers ofpoly(vinyl ester), e.g., $C_1$–$C_6$ vinyl esters, preferably poly(vinyl acetate) grafted onto polyalkylene oxide backbones, such as polyethylene oxide backbones. See European Patent Application 0 219 048, published Apr. 22, 1987 by Kud, et al. Commercially available soil release agents of this kind include the SOKALAN type of material, e.g., SOKALAN HP-22, available from BASF (West Germany).

One type of preferred soil release agent is a copolymer having random blocks of ethylene terephthalate and polyethylene oxide (PEO) terephthalate. The molecular weight of this polymeric soil release agent is in the range of from about 25,000 to about 55,000. See U.S. Pat. No. 3,959,230 to Hays, issued May 25, 1976 and U.S. Pat. No. 3,893,929 to Basadur issued Jul. 8, 1975.

Another preferred polymeric soil release agent is a polyester with repeat units of ethylene terephthalate units contains 10–15% by weight of ethylene terephthalate units together with 90–80% by weight of polyoxyethylene terephthalate units, derived from a polyoxyethylene glycol of average molecular weight 300–5,000. Examples of this polymer include the commercially available material ZELCON 5126 (from Dupont) and MILEASE T (from ICI). See also U.S. Pat. No. 4,702,857, issued Oct. 27, 1987 to Gosselink.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Patent 4,968,451, issued Nov. 6, 1990 to J. J. Scheibel and E. P. Gosselink. Other suitable polymeric soil release agents include the terephthalate polyesters of U.S. Pat. No. 4,711,730, issued Dec. 8, 1987 to Gosselink et al, the anionic end-capped oligomeric esters of U.S. Pat. 4,721,580, issued Jan. 26, 1988 to Gosselink, and the block polyester oligomeric compounds of U.S. Pat. No. 4,702,857, issued Oct. 27, 1987 to Gosselink.

Preferred polymeric soil release agents also include the soil release agents of U.S. Pat. No. 4,877,896, issued Oct. 31, 1989 to Maldonado et al, which discloses anionic, especially sulfoaroyl, end-capped terephthalate esters.

Still another preferred soil release agent is an oligomer with repeat units of terephthaloyl units, sulfoisoterephthaloyl units, oxyethyleneoxy and oxy-1,2-propylene units. The repeat units form the backbone of the oligomer and are preferably terminated with modified isothionate end-caps. A particularly preferred soil release agent of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

If utilized, soil release agents will generally comprise from about 0.01% to about 10.0%, by weight, of the detergent compositions herein, typically from about 0.1% to about 5%, preferably from about 0.2% to about 3.0%.

Other Ingredients—Detersive ingredients or adjuncts optionally included in the instant compositions can include one or more materials for assisting or enhancing cleaning performance, treatment of the substrate to be cleaned, or designed to improve the aesthetics of the compositions. Such materials are further illustrated in U.S. Pat. No. 3,936, 537, Baskerville et al. Adjuncts which can also be included in compositions of the present invention, in their conventional art-established levels for use (generally from 0% to about 20% of the detergent ingredients, preferably from about 0.5% to about 10%), include other active ingredients such as dispersant polymers from BASF Corp. or Rohm & Haas; anti-tarnish and/or anti-corrosion agents, dyes, fillers, optical brighteners, germicides, hydrotropes, enzyme stabilizing agents, perfumes, solubilizing agents, clay soil removal/anti-redeposition agents, carriers, processing aids, pigments, solvents for liquid formulations, fabric softeners, static control agents, etc.

Dye Transfer Inhibiting Agents—The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

More specifically, the polyamine N-oxide polymers preferred for use herein contain units having the following structural formula: R-A$_x$-P; wherein P is a polymerizable unit to which an N—O group can be attached or the N—O group can form part of the polymerizable unit or the N—O group can be attached to both units; A is one of the following structures: —NC(O)—, —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

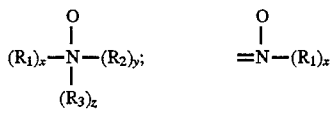

wherein R$_1$, R$_2$, R$_3$ are aliphatic, aromatic, heterocyclic or alicyclic groups or combinations thereof; x, y and z are 0 or 1; and the nitrogen of the N—O group can be attached or form part of any of the aforementioned groups. The amine oxide unit of the polyamine N-oxides has a pKa <10, preferably pKa <7, more preferred pKa <6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide. The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000. This preferred class of materials can be referred to as "PVNO". The most preferred polyamine N-oxide useful in the detergent compositions herein is poly(4-vinylpyridine-N-oxide) which as an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth, et al., Chemical Analysis, Vol 113. "Modern Methods of Polymer Characterization", the disclosures of which are incorporated herein by reference.) The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50: 1, and more preferably from about 3:1 to about 10:1.

If high sudsing is desired, suds boosters such as the C$_{10}$-C$_{16}$ alkanolamides can be incorporated into the compositions, typically at 1%–10% levels. The C$_{10}$-C$_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, for example, 0.1%–2%, to provide additional suds and to enhance grease removal performance.

Brightener—Any optical brighteners, fluorescent whitening agents or other brightening or whitening agents known in the art can be incorporated in the instant compositions when they are designed for fabric treatment or laundering, at levels typically from about 0.05% to about 1.2%, by weight, of the detergent compositions herein. Commercial optical brighteners which may be useful in the present invention can be classified into subgroups, which include, but are not necessarily limited to, derivatives of stilbene, pyrazoline, coumarin, carboxylic acids, methinecyanines, dibenzothiophene-5,5-dioxide, azoles, 5- and 6-membered-ring heterocyclic brighteners, this list being illustrative and non-limiting. Examples of such brighteners are disclosed in "The Production and Application of Fluorescent Brightening Agents", M. Zahradnik, Published by John Wiley & Sons, New York (1982). Specific examples of optical brighteners which are useful in the present compositions are those identified in U.S. Pat. No. 4,790, 856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Artic White CC and Artic White CWD, available from Hilton-Davis, located in Italy; the 2-(4-styryl-phenyl)-2H-naphthol [1,2-d]triazoles; 4,4'-bis- (1 ,2,3-triazol-2-yl)-stilbenes; 4,4'-bis(styryl)bisphenyls; and the aminocoumarins. Specific examples of these brighteners include 4-methyl-7-diethyl-amino coumarin; 1,2-bis(-benzimidazol-2-yl)ethylene; 2,5-bis(benzoxazol-2-yl)thiophene; 2-styryl-napth-[1,2-d] oxazole; and 2-(stilbene-4-yl)-2H-naphtho-[1,2-d]triazole. See also U.S. Pat. No. 3,646,015, issued Feb. 29, 1972 to Hamilton. Anionic brighteners are typically preferred herein.

Coating—Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT®D10, Degussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

The compositions herein can contain other fluids as carders. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carders.

The following examples illustrate the chelants of this invention and cleaning compositions which can be prepared using the chelants along with bleach activators, but are not intended to be limiting thereof. All materials in the Examples satisfy the functional limitations herein.

EXAMPLE I

The following detergent compositions are prepared by mixing:

|  | A | B | C | D |
|---|---|---|---|---|
| Hydrogen Peroxide | 3.0 | 4.0 | 6.0 | 7.5 |
| Bleach Activator* | 3.0 | 3.5 | 3.5 | 7.0 |
| Neodol ™ 45-7** surfactant | 9.0 | 4.0 | 6.0 | 6.4 |
| Neodoll ™ 23-3** surfactant | 0.0 | 9.0 | 9.0 | 8.6 |
| Na $C_{12}$ alkyl sulfate | 0.0 | 2.0 | 0.0 | 2.0 |
| Selected Chelant*** | 2.5 | 1.5 | 1.0 | 0.5 |
| Optional Chelant or Stabilzier**** | 0.0 | 0.0 | 0.1 | 0.2 |
| Brightener | 0.0 | 0.0 | 0.2 | 0.2 |
| Butylated hydroxytoluene | 0.0 | 0.0 | 0.1 | 0.05 |
| Citric Acid | 0.0 | 0.0 | 0.3 | 0.3 |
| Perfume and Dye | 0.0 | 0.0 | 0.5 | 0.5 |
| $H_2SO_4$ | to pH = 4 | to pH = 4 | to pH = 4 | to pH = 4 |
| Water | to balance | to balance | to balance | to balance |

*Bleach activators include acylated trialkylcitrates, nonanoylcaprolactam, nonanoylvalerolactam, octanoylcaprolactam, octanoylvalerolactam, substituted and unsubstituted benzoylcaprolactam and benzoylvalerolactam, including nitrobenzoylcaprolactam and nitrobenzoylvalerolactam.
**Neodol surfactant is available from Shell Chemical Co.
***Selected chelants of the present invention including those of structures I through XX in the Detailed Description.
****Optional soluble chelant or stabilizer to enhance $H_2O_2$ storage stability in product; e.g., diethylene triamine pentaacetic acid, ethylenediaminetetraacetic acid, diethylenetriaminepenta (methylenephosphonic acid), ethylenediaminetetra(methylenephosphonic acid), ethylhydroxydiphosphonic acid, sodium stannate, sodium pyrophosphate.

EXAMPLE II

The selected chelants of the present invention exhibit significantly increased stability in aqueous acidic bleaching compositions, especially over extended storage times. The selected chelants are therefore surprisingly effective upon use of the composition even apter extended storage, resulting in improved bleaching performance of the composition. To illustrate the benefit of the selected chelants, the following compositions are prepared:

TABLE II-1

| Bleaching Compositions | | | |
|---|---|---|---|
| | A | B | C |
| Hydrogen Peroxide | 7.5 | 7.5 | 7.5 |
| Bleach Activator* | 7.0 | 7.0 | 7.0 |
| Neodol ™ 45-7 surfactant | 6.7 | 6.7 | 6.7 |
| Neodol ™ 23-3 surfactant | 8.3 | 8.3 | 8.3 |
| Sodium alkyl sulfate | 2.0 | 2.0 | 2.0 |
| Ethylenebis(2-hydroxyphenyl)glycine** | 0 | 0 | 0.5 |
| Diethylenetriaminepenta(methylenephosphonic acid)*** | 0 | 1.0 | 0 |
| Diethylenetriamainepentaacetic acid**** | 0.1 | 0.1 | 0.1 |
| $H_2SO_4$ | to pH = 4 | to pH = 4 | to pH = 4 |
| Water | to balance | to balance | to balance |

*Bleach activator is acetyl triethylcitrate.
**Selected chelants of the present invention including those of structures I through XX.
***Other secondary chelant.
****Optional secondary chelant at low level.

Addition of each of the compositions in Table II-1 to an aqueous alkaline wash solution (pH=10) immediately after preparation of the composition results in generation of peracetic acid from the reaction of acetyltriethylcitrate with hydrogen peroxide at pH=10. The peracid can be titrated iodometrically, and the percent theoretical yield of available oxygen is determined to be 40% (Table 11-2). Since various metal ions, such as Cu(II), Fe(III), or others, can be present in low but non-negligible concentrations in the wash solution, the presence of a chelating agent capable of sequestering the metal ions is necessary to observe bleaching performance from the present bleaching compositions.

As Table 11-2 shows, little or no available oxygen is observed for composition A with 1.0 ppm Cu(II)SO$_4$ present in the wash solution, and a loss of bleaching performance results. However, the percent theoretical yield of available oxygen for compositions B and C depends on the storage time of the composition. After only 3 months storage time, little or no peracetic acid is titrated from composition B containing 1.0% of diethylenetriamine-penta (methylenephosphonic acid), and a concurrent loss of bleaching performance from this composition results. Coversely, even after 6 months storage, the 40% theoretical yield of available oxygen is still observed from composition C containing the selected chelant, ethylenebis(2-hydroxyphenyl)glycine, of this invention, and good bleaching performance from this composition results. Thus, by the use of a selected chelant, the bleaching performance of the present bleaching compositions can be substantially increased even upon extended product storage.

TABLE II-2

Percent theoretical yield of available oxygen determined by iodometric titration as a function of composition storage time at 20° C.

| Storage time (20° C.) | Composition A | Composition B | Composition C |
|---|---|---|---|
| 0 ppm CuSO$_4$ in solution | | | |
| 1 day | 40% | 40% | 40% |
| 3 months | 40% | 40% | 40% |
| 6 months | 40% | 40% | 40% |
| 1.0 ppm CuSO$_4$ in solution | | | |
| 1 day | <5% | 40% | 40% |
| 3 months | <5% | <5% | 40% |
| 6 months | <5% | <5% | 40% |

What is claimed is:

1. A liquid, aqueous detergent composition having a pH of below about 7 and comprising
   a) an bleaching effective amount of a source of hydrogen peroxide;
   b) at least about 0.05% of a chelant, which is substantially undissolved at the pH of said detergent composition, of the formula

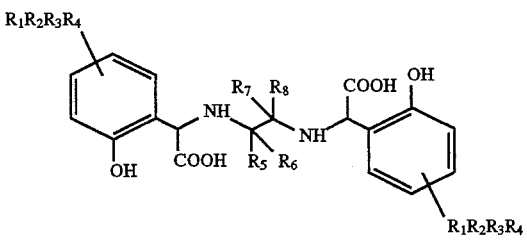

wherein $R_1$, $R_2$, $R_3$, and $R_4$ are independently selected from the group consisting of —H, alkyl, alkoxy, aryl, aryloxy, —Cl, —Br, —NO$_2$, —C(O)R', and —SO$_2$R"; further wherein R' is selected from the group consisting of —H, —OH, alkyl, alkoxy, aryl, and aryloxy; R" is selected from the group consisting of alkyl, alkoxy, aryl, and aryloxy; and $R_5$, $R_6$, $R_7$, and $R_8$ are independently selected from the group consisting of —H and alkyl; and c) about 0.01 to about 50% by weight of a detersive surfactant.

2. A liquid, aqueous detergent composition according to claim 1 wherein $R_1$, $R_2$, $R_3$, and $R_4$ are independently selected from the group consisting of—H, alkyl, and alkoxy; and $R_5$, $R_6$, $R_7$, and $R_8$ are independently selected from the group consisting of —H and methyl.

3. A liquid, aqueous detergent composition according to claim 2 wherein $R_1$, $R_2$, $R_3$, and $R_4$ are independently selected from the group consisting of—H and methyl; and $R_5$, $R_6$, $R_7$, and $R_8$ are —H.

4. A liquid, aqueous detergent composition according to claim 1 further comprising a bleach activator.

5. A liquid, aqueous detergent composition according to claim 4 wherein said bleach activator is selected from the group consisting of acylated trialkylcitrates, N-acyl caprolactams, N-acyl valerolactams, and mixtures thereof.

6. A liquid, aqueous detergent composition according to claim 1 wherein said chelant is present in an amount of from about 0.05% to about 5%, by weight of detergent composition.

7. A liquid, aqueous detergent composition according to claim 6 wherein said pH is from about 3 to about 7.

8. A liquid, aqueous detergent composition according to claim 6 wherein said chelant has a particle size of from about 0.1 to about 1,000 microns.

9. A liquid, aqueous detergent composition according to claim 8 having a rheology capable of suspending solids.

10. A liquid, aqueous detergent composition according to claim 6 further comprising optional conventional detersive additives.

11. A liquid, aqueous detergent composition according to claim 10 wherein said optional conventional detersive additives comprises a secondary conventional chelant.

12. A liquid, aqueous detergent composition according to claim 11 wherein said secondary conventional chelant is selected from the group consisting of diethylene triamine pentaacetie acid, diethylene triamine penta(methylene phosphonic acid), sulfonated ethylenebis(2-hydroxyphenyl) glycine, and mixtures thereof.

13. A liquid, aqueous detergent composition according to claim 10 wherein said optional conventional detersive additives comprises inorganic stabilizers.

14. A liquid, aqueous detergent composition according to claim 10 wherein said optional conventional detersive additives comprises an antioxidant or a radical scavenger.

15. A liquid, aqueous detergent composition according to claim 1 wherein said chelant is of the structures:

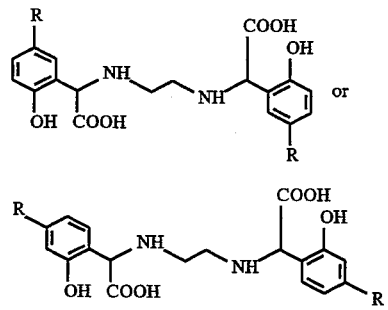

wherein each R is independently selected from the group consisting of—H, —$CH_3$, $C_2$-$C_9$ alkyl, and mixtures thereof.

16. A liquid, aqueous detergent composition according to claim 15 wherein said chelant is of the structures:

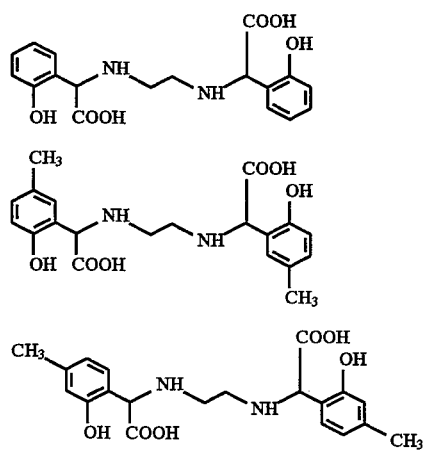

* * * * *